United States Patent [19]

Jennings, Jr.

[11] Patent Number: 4,650,468
[45] Date of Patent: Mar. 17, 1987

[54] MEDICAL SYRINGE

[76] Inventor: Baldwin P. Jennings, Jr., 330 Sharon La., Staunton, Va. 24401

[21] Appl. No.: 833,045

[22] Filed: Feb. 26, 1986

[51] Int. Cl.⁴ ............................................. A61M 5/00
[52] U.S. Cl. .................................... 604/110; 604/194
[58] Field of Search .............. 604/110, 111, 194, 195, 604/218, 220, 228, 198, 192

[56] References Cited

U.S. PATENT DOCUMENTS

| 2,888,923 | 6/1959 | Reis | 604/194 |
| 3,584,626 | 6/1971 | Johansson | 604/194 X |
| 4,562,844 | 1/1986 | Carpenter et al. | 604/220 X |
| 4,573,976 | 3/1986 | Sampson et al. | 604/198 |

Primary Examiner—John D. Yasko
Attorney, Agent, or Firm—B. P. Fishburne, Jr.

[57] ABSTRACT

A single use disposable medical syringe is constructed and operated in a manner which prevents transmission of infection by the syringe after its use for inoculation. The syringe is marketed in a sterile package ready for use. The syringe needle is then covered by a shield. The syringe plunger assembly is then releasably locked to the barrel of the syringe. Following opening of the sterile package and removal of the needle shield, the plunger assembly is operated to fill the syringe barrel with medication and to inject the patient. Following injection, a piston head housing is unlocked from the syringe barrel and the plunger assembly is retracted toward the rear of the barrel and becomes automatically locked in this position with the piston head housing. The needle is disposed within the barrel rearwardly of a safety shield on the forward end of the barrel containing a safety membrane.

10 Claims, 7 Drawing Figures

MEDICAL SYRINGE

BACKGROUND OF THE INVENTION

Infectious diseases, such as AIDS and serum hepatitis, have created an urgent need for a reliable, practical and convenient anti-contaminating medical syringe. Such a syringe must be relatively inexpensive to manufacture, rendering it disposable after a single injection or usage.

The objective of the present invention is to fully satisfy the need for an anti-contaminating syringe in terms of fully protecting the patient, medical personnel and innocent third parties against the possibility of infection being transmitted by the syringe.

Toward this end, the syringe according to the present invention is provided in a sterile, easily openable package and is pre-adjusted so that it is ready to be used for injecting a patient after removal from the sterile package and after separation of a removable shield from the forward end of the syringe which encloses the syringe needle prior to use.

The syringe is operated conventionally to draw liquid medication from a bottle having an elastic diaphragm or stopper and to then inject the patient.

A housing element within which a piston head of the syringe plunger assembly is captured and which is locked to the forward end of the syringe barrel prior to and during normal usage of the syringe is unlocked by a twisting action of the plunger assembly and is then retracted with the plunger assembly toward the rear of the syringe barrel where such assembly, including the piston head housing, becomes automatically positively locked to effectively prevent reuse of the syringe. In this retracted position, the syringe needle is held inside of the barrel rearwardly of a safety shield on the forward end of the barrel containing an elastic membrane through which the needle projected prior to and during the injection process. The retracted needle cannot be touched nor can the membrane in the safety shield be touched, thus rendering the transmission of infection by the syringe virtually impossible.

Other features and advantages of the syringe according to the present invention will become apparent to those skilled in the art during the course of the following description.

DETAILED DESCRIPTION

Figure 1:
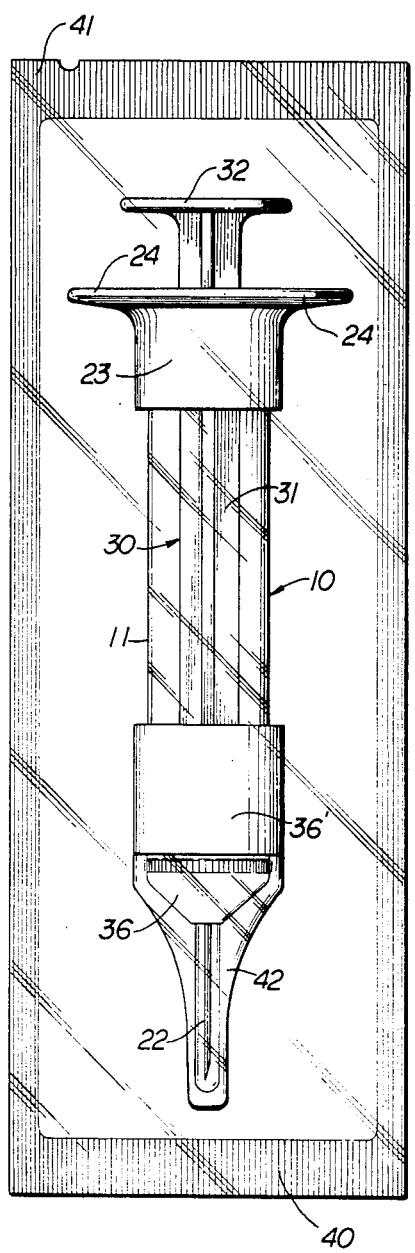
FIG. 1 is a side elevation of a syringe and sterile package according to the present invention with the syringe conditioned for usage following removal from the sterile package and separation of a needle shield from the syringe.

Referring to the drawings in detail wherein like numerals designate like parts, a single-use disposable medical syringe 10 according to the invention comprises a syringe barrel 11 provided slightly rearwardly of its forward end with a pair of internal diametrically opposed locking lugs 12. A cylindrical piston head housing 13 having spaced end walls 14 and 15 receives a piston head well 16 captively therein, the well being held or captured between the two end walls 14 and 15 of the housing 13.

The well 16 has a cavity 17, preferably in the shape of a downwardly tapered truncated pyramid adapted to receive through its top a piston head 18 of like shape which nests within the cavity 17. The piston head 18 enters and leaves the cavity 17 through an opening 19 formed in the end wall 14 of the housing 13. The housing 13 contains therein a pair of diametrically opposite stop lugs 20 which resist rotation of the well 16 in the housing 13 beyond prescribed limits. The housing 13 is provided in its cylindrical side wall at diametrically opposite points with bayonet locking slots 21, adapted to receive and release the locking lugs 12 in response to twisting of the housing 13 within the barrel 11, as will be further explained. A tubular pointed syringe needle 22 is secured to the end wall of the well 16 with its bore in communication with the cavity 17 of the well.

The syringe further comprises a disc housing 23 fixed to the rear end of the barrel 11 and having opposite side finger grips 24. The housing 23 has a serrated bore 25 receiving therein snugly but rotationally an externally serrated friction disc 26 having a cruciform opening 27. A plunger lock ring 28 is fixed in the housing 23 and is provided at diametrically opposite points with a pair of internal spring locking tabs 29, whose purpose will be described.

A syringe plunger assembly 30 includes a straight elongated cruciform plunger stem 31 which engages somewhat loosely through the cruciform opening 27 of the friction disc 26. The rear end of the plunger 31 is equipped with a thumb plate 32.

The plunger assembly further includes near the forward end of the stem 31 a piston 33 equipped with an O-ring 34. The piston 33 is fixed on the stem 31 somewhat rearwardly of the piston head 18 which forms a part of the plunger assembly 30.

A plunger assembly locking disc 35 is also fixed to the stem 31 somewhat rearwardly of the piston 33 and is sized to pass freely through the syringe barrel 11 when the plunger assembly is shifted longitudinally of the barrel 11. The piston O-ring 34 sealingly wipes the bore of the barrel 11.

Figure 2:
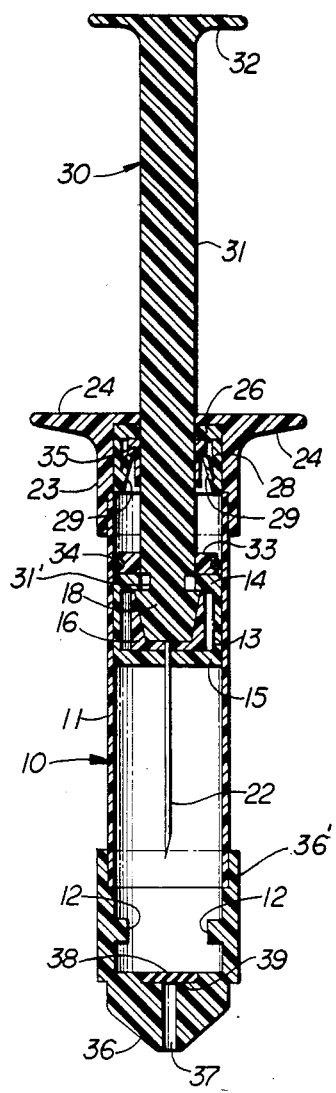
FIG. 2 is a longitudinal vertical section taken through the syringe with its plunger assembly locked in a retracted safety position ready for disposal following a single use.
Figure 3:
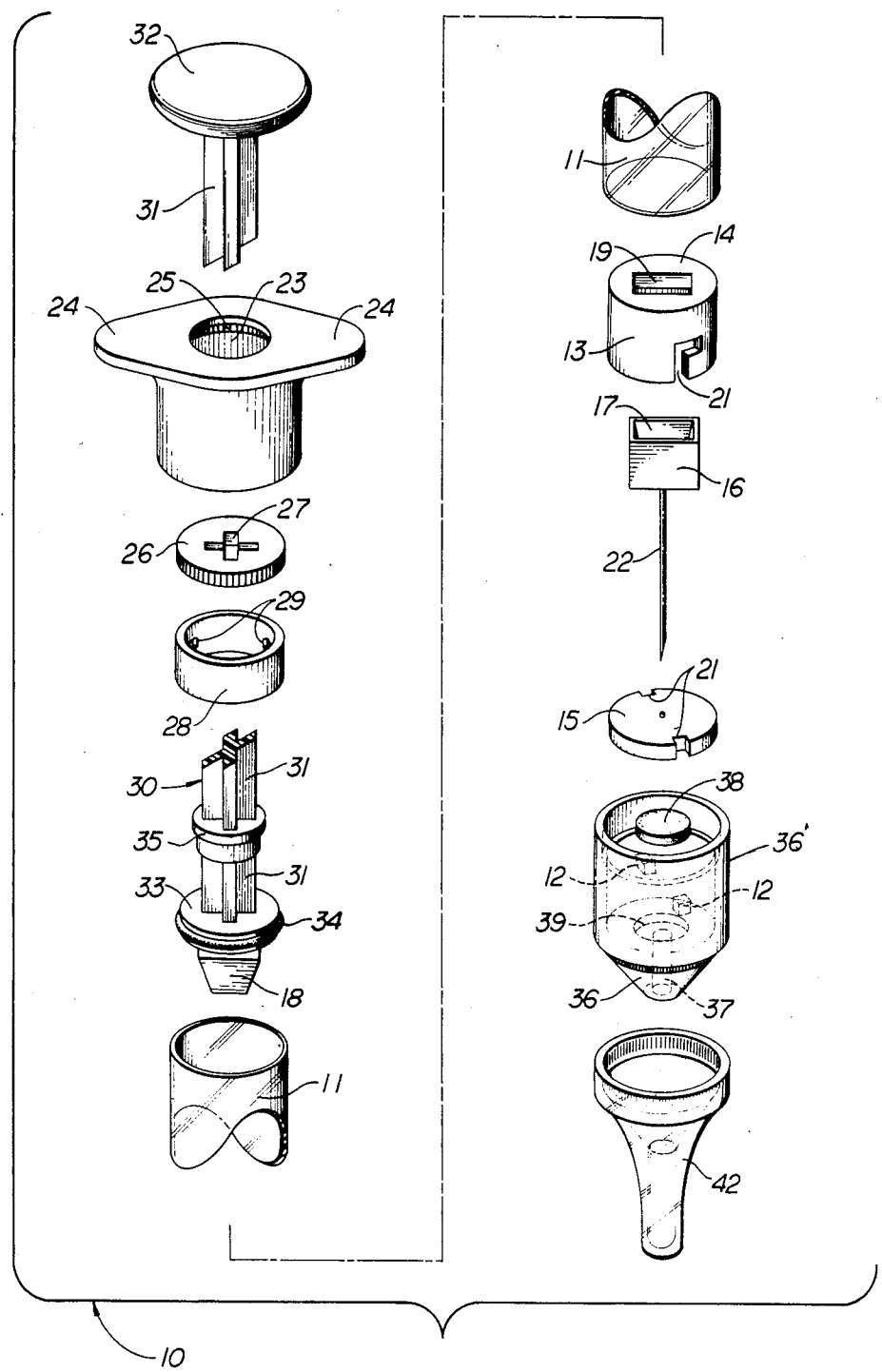
FIG. 3 is an exploded perspective view of the syringe, partly broken away.

As will be further described, when the plunger assembly 30 is retracted to its locked safety position as shown in FIG. 2, the locking disc 35 enters the plunger locking ring 28 and depresses the spring locking tabs 29 which then snap back to their normal positions in front of the disc 35, FIG. 2, to lock the plunger assembly 30 in the safety retracted position, thereby preventing reuse of the syringe.

The syringe further comprises a forward end tapered safety shield 36 having a narrow needle clearance opening 37 and a rearward rubber or rubber-like membrane 38 held firmly within a seating recess 39 at the rear of the shield 36. The needle safety shield 36 is fixed to the forward end of the syringe barrel 11 by a sleeve portion 36' to which the lugs 12 are preferably attached. Prior to use of the syringe for injecting a patient, the needle 22 penetrates the rubber membrane 38 and projects entirely through and beyond the safety shield 36, FIGS. 1 and 4. Following use of the syringe for making an injection and following retraction of the plunger assembly 30, FIG. 2, the needle 22 is bodily inside of the barrel 11 and well rearwardly of the membrane 38 from which it has been withdrawn. Hence, no one can touch the retracted needle 22 or the membrane 38, which is at the rear of the safety shield 36.

As shown in FIG. 1, the syringe prior to use is enclosed in a conventional sterile package 40 having a tear-away corner 41 to facilitate opening the package. Within the sterile package, the syringe carries an easily removable needle shield 42, which is removed from the syringe to expose the needle after the syringe is taken from the sterile package.

OPERATION

As previously explained, the syringe 10 as taken from the sterile package 40 is ready for use after removal of the needle shield 42. The piston head housing 13 is locked to the front of the barrel 11 by the lugs 12 and bayonnet locking slots 21. The well 16 is captively held in the housing 13 and the piston head 18 is nested in the mating cavity 17 of the well 16.

The needle 22 is now inserted through the diaphragm or stopper of a medicine bottle and the plunger assembly 30 is retracted to draw liquid into the barrel 11. During this operation, the piston 33 produces the necessary suction in the syringe barrel to draw in the liquid medication. The piston head housing 13 remains locked in the forward position, FIG. 4, and the well 16 is still captively held by the housing 13. However, the tapered piston head 18 can move rearwardly with the rest of the plunger assembly 30 and can exit the housing 13 through the provided opening 19.

Figure 4:
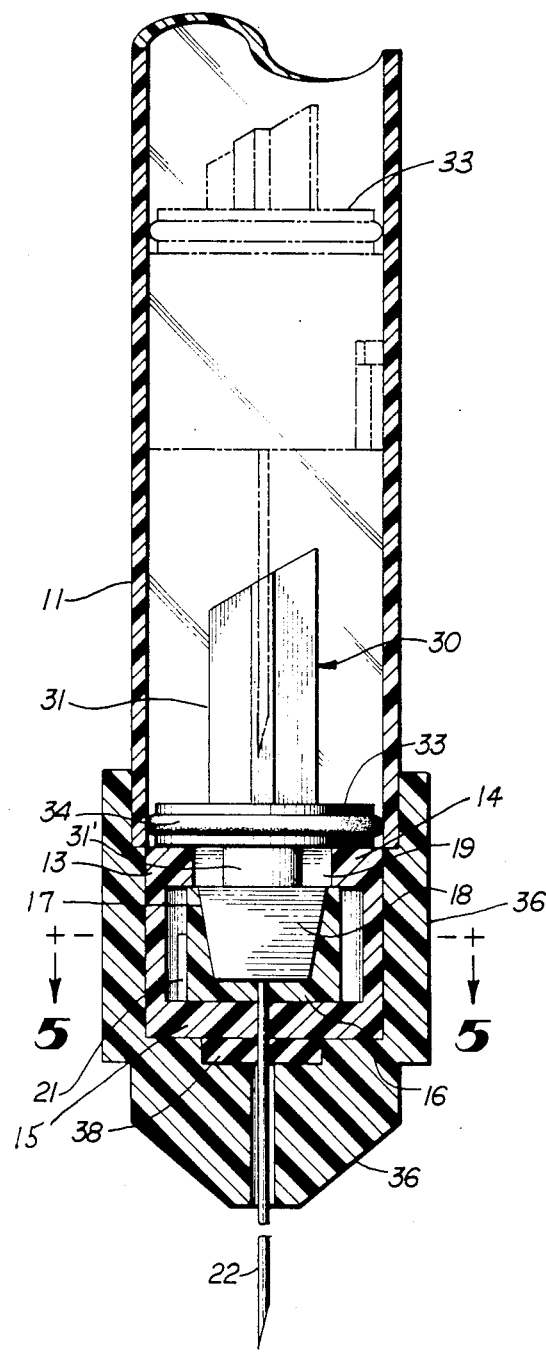
FIG. 4 is an enlarged fragmentary longitudinal vertical section taken through the syringe with its plunger assembly in a forwardmost position.

The injection or innoculation is now carried out by thrusting the plunger assembly 30 forwardly, during which the piston 33 forces the liquid into and through the needle 22 which is penetrating the tissue of a patient. At the end of the forward movement of the piston assembly, the head 18 passes through the opening 19 and is again received in the cavity 17, as shown in FIG. 4.

Figure 6:
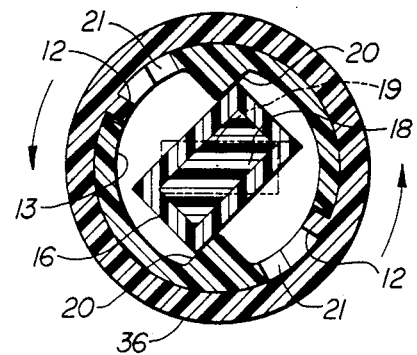
FIGS. 6 and 7 are similar sections depicting stages of rotation of the plunger assembly relative to and with a piston head housing.
Figure 7:
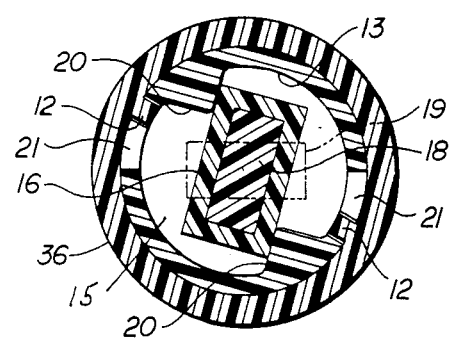

Following this, the plunger assembly 30 is rotated on its longitudinal axis, causing the piston head 18 to turn the well 16 an amount limited by the two stops 20 of housing 13. When these stops are engaged by the well 16 as shown in FIG. 6, the housing 13 begins to turn, as shown in FIG. 7, and the housing rotates relative to the barrel 11 and the sleeve portion 36' attached to safety shield 36. This rotation allows separation of the two lugs 12 from the housing 13 by passing through the bayonnet locking slots 21 thereof which in turn allows retraction of the plunger assembly 30 with the housing 13 toward the rear of the barrel 11, as shown in FIG. 2.

During this movement, the locking disc 35 on plunger stem 31 trips over and behind the spring locking tabs 29 and the plunger assembly and housing 13 become securely locked in the safe retracted position with the needle 22 completely enclosed in the syringe barrel 11 well rearwardly of the membrane 38. The plunger assembly 30 cannot again be pushed forwardly because the locking means 29, etc. is non-releasable. The syringe is now disposed of in a proper manner, and the possibility of spreading infection with the syringe is rendered nil.

Except for the needle 22, the disposable syringe can be formed from inexpensive plastics materials and rubber.

Figure 5:
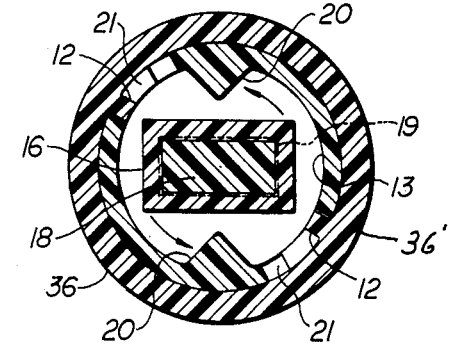
FIG. 5 is a transverse horizontal section taken on line 5—5 of FIG. 4.

It has not been previously described that the plunger stem 31 has a short cylindrical portion 31' between the piston head 18 and piston 33, FIGS. 2 and 4. This short cylindrical portion is necessary to enable rotation of the stem 31 relative to the housing 13 prior to the turning and unlocking of the latter to enable retraction of the assembly to the safety locking position shown in FIG. 2. The initial rotation of the stem 31 relative to the housing 13 enabled by the cylindrical portion 31' is depicted in FIGS. 5 and 6.

Again referring to the friction disc 26, this disc has two functions in the invention. First, it provides alignment and guidance of the stem 31 and the elements attached thereto, and secondly, the friction disc allows rotation of the stem 31 and plunger assembly relative to the disc housing 23 which is fixed on the barrel 11.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A medical syringe comprising a syringe barrel, a safety shield on the forward end of the syringe barrel including an elastic membrane spaced substantially rearwardly from the forward end of the safety shield, a piston head housing, means releasably locking the piston head housing in the forward end portion of the syringe barrel immediately behind the safety shield, a plunger assembly for the syringe comprising a plunger shank, a polygonal cross section piston head on the forward end of said shank, a piston element on the shank rearwardly of the piston head wipingly sealingly engaging the bore of said barrel, a piston head well carrying a needle and being captively held within said piston head housing and having a cavity receiving said piston head and having a polygonal cross sectional shape matching the shape of the piston head, stop means within the piston head housing to limit rotation of the piston head well therein, a disc housing fixed on the rear end of said barrel, a friction disc snugly rotationally held within the friction disc housing and having a geometric non-circular opening formed therethrough, said plunger shank being received through said geometric non-circular opening and having a matching cross sectional shape, whereby rotation of said shank will rotate said friction disc, said piston head and piston head well and said piston head housing to release the latter from said barrel, a locking disc fixed on said shank somewhat rearwardly of said piston element and being movable with said shank through the bore of said barrel, and a non-releasable locking means for said locking disc fixed to the rear end portion of said barrel immediately forwardly of said disc housing and being engageable with the locking disc in response to retracting of said stem to lock the plunger assembly including said piston head housing in a safety retracted position on said barrel with said needle enclosed by the barrel rearwardly of said safety shield and elastic membrane, and said needle piercing the elastic membrane and extending forwardly thereof through the safety shield prior to usage of the syringe.

2. A medical syringe as defined in claim 1, and a sterile package means completely enclosing said syringe prior to use thereof and prior to the opening of said package.

3. A medical syringe as defined in claim 2, and a readily removable needle enclosing shield on the syringe within said sterile package and prior to using the syringe.

4. A medical syringe as defined in claim 1, and said piston head being captively held within the piston head housing between two end walls of the housing, one of which end walls has an opening adapted to receive said piston head therethrough so that the piston head may enter the cavity of said piston head well.

5. A medical syringe as defined in claim 1, and the first-named means comprising internal locking lugs on said barrel near the forward end of the barrel, and cooperative locking slots in the side wall of the piston head housing.

6. A medical syringe as defined in claim 5, and said locking slots comprising bayonet slots.

7. A medical syringe as defined in claim 1, and the polygonal cross section piston head comprising a forwardly tapering truncated pyramid head.

8. A medical syringe as defined in claim 7, and said plunger shank having cruciform cross section, said friction disc having a cruciform opening formed therethrough receiving said shank.

9. A medical syringe comprising a syringe barrel, a safety shield on the forward end of said barrel including an elastic membrane adapted to be penetrated by a needle of the syringe, a piston head housing rotationally releasably locked within the forward end portion of the syringe barrel, a piston head well having a non-circular cross section and a non-circular cavity disposed captively within the piston head housing and adapted for limited rotation only therein on the longitudinal axis of the syringe, a syringe plunger having a shank and a non-circular piston head on the forward end of the shank engageable within the cavity of said well, the piston head housing including a rear end wall having an opening through which the piston head can enter said cavity and leave the cavity, a piston element fixed on said shank rearwardly of said piston head and said piston head housing, a locking disc fixed on said shank rearwardly of said piston element, and a non-releasable locking means for said locking disc fixed on the rear end portion of the syringe barrel whereby the syringe plunger is lockable in a safety retracted position with the needle of the syringe enclosed by said barrel rearwardly of said safety shield and membrane, and said needle being attached to the forward end of said piston head well in communication with the cavity thereof.

10. A medical syringe comprising a syringe barrel, a first non-releasable syringe plunger locking means at the rear end of said barrel and being fixed relative thereto, a safety shield fixed on the syringe barrel at the forward end thereof and having a safety needle pierceable membrane, a second releasable syringe plunger locking means fixed on the syringe barrel substantially at its forward end and somewhat rearwardly of said safety shield and membrane, a syringe plunger assembly guidably engaged in the syringe barrel and being longitudinally movable and turnable therein, said plunger assembly including a stem, a piston element fixed on said stem and a locking element fixed on said stem somewhat rearwardly of the piston element and being engageable with said first non-releasable syringe plunger locking means, a piston head on said stem forwardly of the piston element, a piston head well having a cavity adapted to receive the piston head therein removably, a syringe needle secured to said well, and a piston head housing movably disposed in said barrel and substantially surrounding and captively holding said well and having an opening through which said piston head can enter and exit the piston head housing and well, and cooperative releasable locking means on the piston head housing and being engageable with said second releasable syringe plunger locking means.

* * * * *